(12) United States Patent
Reichow et al.

(10) Patent No.: US 8,282,209 B2
(45) Date of Patent: Oct. 9, 2012

(54) SYSTEMS AND METHODS FOR TESTING AND/OR TRAINING NEAR AND FAR VISUAL ABILITIES

(75) Inventors: Alan W. Reichow, Beaverton, OR (US); Ryan C. Coulter, Portland, OR (US)

(73) Assignee: Nike, Inc., Beaverton, OR (US)

( * ) Notice: Subject to any disclaimer, the term of this patent is extended or adjusted under 35 U.S.C. 154(b) by 154 days.

(21) Appl. No.: 12/595,206

(22) PCT Filed: Apr. 14, 2008

(86) PCT No.: PCT/US2008/060237
§ 371 (c)(1),
(2), (4) Date: Mar. 24, 2010

(87) PCT Pub. No.: WO2008/128183
PCT Pub. Date: Oct. 23, 2008

(65) Prior Publication Data
US 2010/0182565 A1  Jul. 22, 2010

Related U.S. Application Data

(60) Provisional application No. 60/923,434, filed on Apr. 13, 2007, provisional application No. 60/941,915, filed on Jun. 4, 2007.

(51) Int. Cl.
*A61B 3/00* (2006.01)
(52) U.S. Cl. .................. 351/203; 351/237; 351/246
(58) Field of Classification Search ................ 351/203, 351/222, 223, 237, 239, 246
See application file for complete search history.

(56) References Cited

U.S. PATENT DOCUMENTS

| | | | |
|---|---|---|---|
| 3,861,790 | A | 1/1975 | Tamura |
| 4,294,522 | A | 10/1981 | Jacobs |
| 4,618,231 | A | 10/1986 | Genco et al. |
| 5,530,492 | A | 6/1996 | Ron |
| 5,539,481 | A * | 7/1996 | Vax ............................. 351/203 |
| 5,825,460 | A | 10/1998 | Kohayakawa |
| 6,454,412 | B1 | 9/2002 | Torrey |
| 2006/0244915 | A1 | 11/2006 | Clemons |
| 2007/0200927 | A1 | 8/2007 | Krenik |

OTHER PUBLICATIONS

International Search Report and Written Opinion of the International Searching Authority; App. No. PCT/US08/60237; Sep. 4, 2008.
China Office Action; App. No. 200880011994; Dated Mar. 9, 2011.
Rouse, et al., "A Comparison Study of Dynamic Visual Acuity Between Athletes and Nonathletes", Journal of the American Optometric Association, Dec. 1988, pp. 946-950, vol. 59, No. 12, United States.

(Continued)

*Primary Examiner* — Huy K Mai
(74) *Attorney, Agent, or Firm* — Shook, Hardy & Bacon L.L.P.

(57) ABSTRACT

Systems and methods for automated testing and/or training of a subject's visual ability at varying distances are provided. A near display device may display visual indicia possessing characteristics. After receiving an input identifying a visual characteristic possessed by the displayed indicia, a second indicia may be displayed on a far display device. After receiving an input identifying a characteristic of the indicia displayed on the far display device, further testing may proceed alternating between the near display device and the far display device. More than two display devices may be utilized, with the display devices being located at differing distances or positions relative to a subject.

13 Claims, 7 Drawing Sheets

OTHER PUBLICATIONS

Koenig, "Practicing Perception: Eyes Can Be Trained to be More Effective", USA Today Baseball Weekly, 1996, 3 pages, United States.

Coffey, et al, "Visual Performance Enhancement in Sports Optometry", Sports Vision 1995, pp. 158-177, Butterworth-Heinermann, United States.

Coffey, et al., "Optometric Evaluation of the Elite Athlete," Problems in Optometry, Mar. 1990, pp. 32-59, vol. 2, No. 1, United States.

Ferreira, "An Overview of Research in Sports Vision: its History and an Optometric Perspective", The South African Optometrist, Dec. 2003, pp. 142-149, vol. 62, No. 4, Auckland Park, South Africa.

Reichow, et al., "Introduction to Behavioral Optometry", Sports Vision, 1993, 75 pages, Optometric Extension Program Foundation, United States.

Supplementary European Search Report, application No. EP 08 74 5771, 8 pages, (1996).

* cited by examiner

SYSTEMS AND METHODS FOR TESTING AND/OR TRAINING NEAR AND FAR VISUAL ABILITIES

CROSS-REFERENCE TO RELATED APPLICATIONS

This application claims priority to U.S. Provisional Application No. 60/923,434 filed on Apr. 13, 2007, entitled "System and Method for Testing Visual Ability During Simulated Activity," which is hereby incorporated by reference. This application also claims priority to U.S. Provisional Application No. 60/941,915 filed on Jun. 4, 2007, entitled "System and Method for Decoupled Visual Ability Testing," which is hereby incorporated by reference.

STATEMENT REGARDING FEDERALLY SPONSORED RESEARCH OR DEVELOPMENT

Not applicable.

TECHNICAL FIELD

The present invention relates to testing and/or training visual abilities. More particularly, the present invention relates to the testing and/or training of the visual abilities of a subject in tasks involving the shifting of visual focus from near to far fields of vision and vice versa.

BACKGROUND OF THE INVENTION

Numerous systems and methods exist to test and, in some instances, train the visual abilities of individuals. One area of visual testing measures a subject's ability to focus on visual stimuli at different distances from the subject. Often, such testing requires a subject to attempt to identify a visual indicia displayed relatively near the subject and to subsequently identify a visual indicia visually distant from the subject. Often, the visual indicia visually far from the subject will be located at optical infinity, meaning that the eyes must completely relax and both look straight ahead of a subject's head to focus on the distant visual indicia. In such testing, a subject may typically alternatively read indicia displayed on a near display and indicia displayed on a far display, with a test administrator recording the accuracy of the subject's identification of indicia. Such a testing approach renders quantifiable response times difficult to obtain. Also problematically, such an approach to testing can permit a subject to read multiple indicia at any given distance, commit the indicia to short-term memory, and then quickly identify alternating indicia without having to focus again on a display at a given distance, thereby further undermining the accuracy of any measurement of the time required for a subject to shift his or her focus on an indicia displayed at a given distance.

SUMMARY OF THE INVENTION

The present invention provides systems and methods to test and/or train the near and far visual focusing abilities of a subject. A first display device may be positioned near to a subject, and a second display device may be positioned far from a subject. An automated voice detection system may be used to detect responses from a subject indicating that the subject has perceived a displayed visual indicia. A second visual indicia at a second distance will not be displayed until a response is received from the subject or, optionally, after the display of the first indicia has timed out. In this fashion, individual indicia at different distances from the subject may be individually displayed in an alternating fashion. The display of only an individual indicia prevents the subject from effectively memorizing multiple indicia at a given distance, thereby providing an accurate measure of the time required for a subject to shift his or her focus to an indicia at a new distance.

BRIEF DESCRIPTION OF THE DRAWING

The present invention is described in detail below with reference to the attached drawing figures, wherein.

DETAILED DESCRIPTION OF THE INVENTION

Systems and methods in accordance with the present invention may be used to test and/or train the visual abilities of a subject in changing the subject's focus from near to far and far to near. Systems and methods in accordance with the invention may utilize at least one near display device and at least one far display device. A far display device may be located at or near optical infinity from a subject. A near display device may be located at differing distances from a subject, ranging from a few inches to several feet. Additionally, multiple display devices at multiple distances may be used, such as a near display device, a far display device, and a mid-range display device located between the near display device and the far display device. Also, multiple near display devices and/or multiple far display devices may be used. Further, display devices may be located in differing directions from a subject. For example, the angle of vision of display devices may differ, with some to the left of a subject's line of vision and some to the right of a subject's line of vision. Display devices may also be positioned higher or lower than the subject's normal line of vision. One skilled in the art will appreciate that different positioning of display devices may be suitable for testing and/or training individuals for particular activities. For example, a baseball shortstop might have to quickly shift visual focus from a batter striking a pitched ball (essentially at optical infinity) to a position towards the ground at approximately the shortstop's knees to field a ground ball. For this reason, visual testing and/or training of an individual playing shortstop might focus on the individual's abilities to focus visually in those two positions. The various aspects of systems and methods in accordance with the present invention are described more fully in association with the attached figures.

Figure 1:
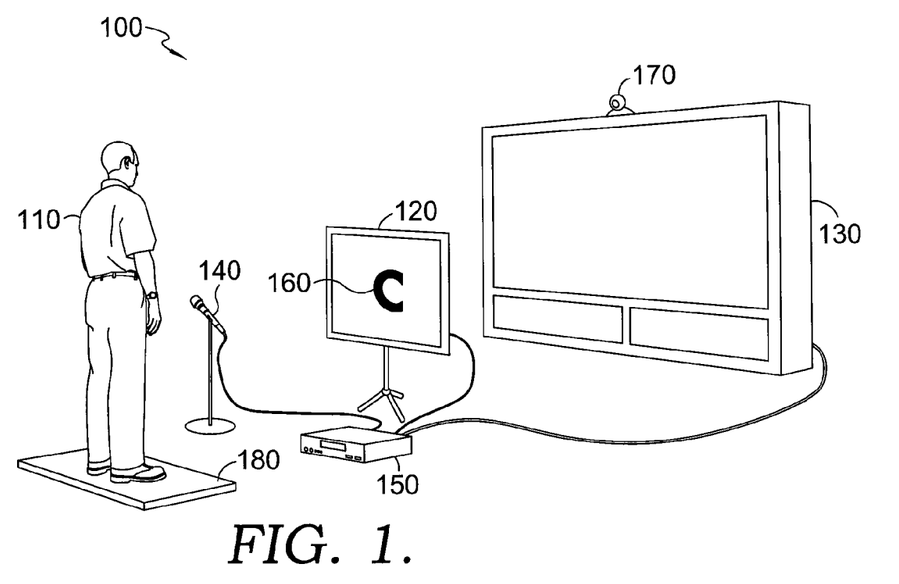
FIG. 1 is an illustration of a system for near far testing in accordance with the present invention.

Referring now to FIG. 1, a system 100 for testing and/or training the near and far visual abilities of a subject is illustrated. A first display device 120 (also referred to as the near display device) may be located visually near to subject 110. The precise distance from subject 110 to near display device 120 may vary depending upon the particular visual ability to be tested or trained, but will be less than optical infinity. A second display device 130 may be located visually far from subject 110. Second display device 130, alternatively referred to as the far display device 130 or distant display device 130, may be located at or near optical infinity relative to subject 110. A microphone 140 may receive spoken responses from subject 110 in response to visual indicia displayed on near display device 120 and/or far display device 130. A testing unit 150 may connect to near display device 120, far display device 130, and microphone 140, as well as other equipment such as a camera 170 and/or pressure sensitive platform 180, which will be described further below: Testing unit 180 may control the display of indicia and the receipt of responses from subject 110. One skilled in the an will appreciate that testing unit 150 may be a computer, such as a personal computer or a gaming device, or other specialized computing device.

One skilled in the art will appreciate and understand that subject 110 may provide any suitable type of input in response to the displayed visual indicia. For example, in another embodiment of the present invention, subject 110 may provide responses using a motor input device. Motor input device may be any device, such as a joystick or keypad, capable of receiving manual input from subject 110, and may also be any device capable of receiving input from any other type of physical action by subject 110, such as foot actuated pedals or buttons. Examples of appropriate devices for use as an input device include keyboards or keypads, buttons, joysticks, switches, pedals, or any other device capable of receiving an active input from subject 110.

As illustrated in FIG. 1, an indicia 160 may be displayed on near display device 120. As illustrated in FIG. 1, indicia 160 comprises a Landolt C. A Landolt C may be used because they are visually neutral indicia that may possess a trait, namely orientation to either the right, left, top, or bottom, that are easily recognized by subjects. As illustrated in FIG. 1, the Landolt C of indicia 160 is oriented to the right as viewed by subject 110.

As illustrated in FIG. 1, system 100 may further utilize a camera 170 to monitor the movements of subject 110 during testing and/or training. Camera 170 may further be devoted to tracking eye movement of subject 110 to correlate eye movement data with the responses given by subject 110 to the display of various indicia on near display device 120 and/or far display device 130. Still referring to FIG. 1, system 100 may further utilize a pressure sensitive platform 180 upon which subject 110 stands during testing and/or training. Pressure sensitive platform 180 may detect shifts in the balance of subject 110 during testing and/or training, which may then be correlated by testing unit 150 to the responses of subject 110 to indicia displayed on near display device 120 and/or far display device 130.

Figure 2:
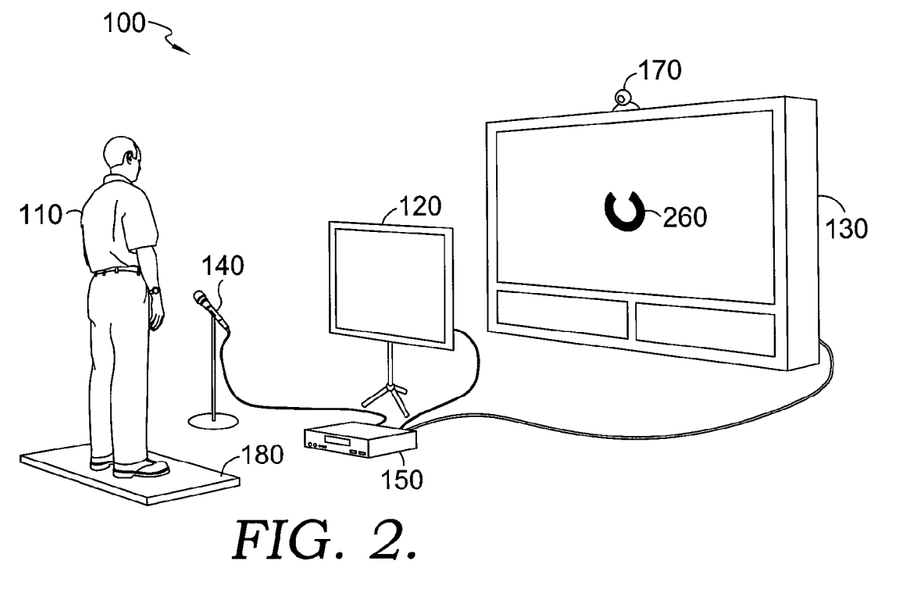
FIG. 2 further illustrates a system for near far testing in accordance with the present invention.

Referring now to FIG. 2, system 100 is illustrated with indicia 160 removed from near display device 120. For example, subject 110 may have correctly identified the indicia 160 displayed in FIG. 1 as oriented to the right, by example by speaking the word "right" into microphone 140. Upon receiving a correct input, or alternatively upon receiving an incorrect input or receiving no input during a pre-determined amount of time, testing unit 150 may remove the display of an indicia upon near display device 120 and commence the display of an indicia 260 on far display device 130. In the example illustrated in FIG. 2, indicia 260 is a Landolt C, this time with an orientation towards the top. Of course, one of ordinary skill in the art will appreciate that the orientation of the Landolt C shown as indicia 260 may vary from that shown and described herein. One skilled in the art will further appreciate that indicia other than Landolt C's, as illustrated in FIG. 1 and FIG. 2 may be used in accordance with the present invention. For example, numerals, letters, pictures, photographs, or other types of indicia that may be recognized by a subject 110 may be utilized.

Figure 3A:
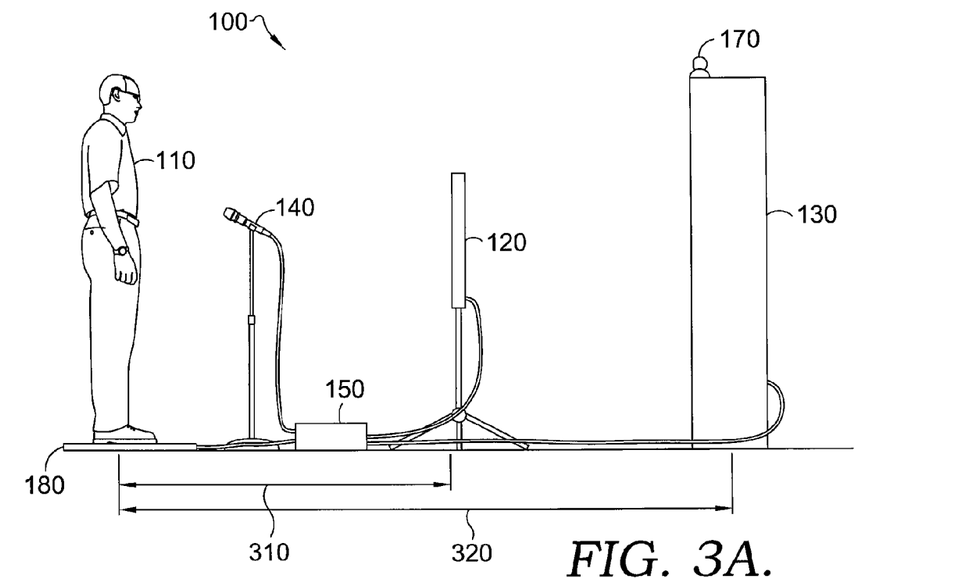
FIG. 3A further illustrates a system for near far testing in accordance with the present invention.

Referring now to FIG. 3A, a further view of system 100 is illustrated. In system 100 near display device 120 is positioned at a first distance 310 from subject 110. As further illustrated in FIG. 3A, near display device 120 is elevated to height approximately at eye level of subject 110. One skilled in the art will appreciate that other elevations and distances are possible, both for near display device 120 and far display device 170. Far display device 170 being located at a second distance 320 from subject 110. One skilled in the art will further appreciate that near display device 120 and far display device 130, as well as additional display devices (not illustrated) if used may be positioned at differing angles of view relative to subject 110.

Figure 3B:
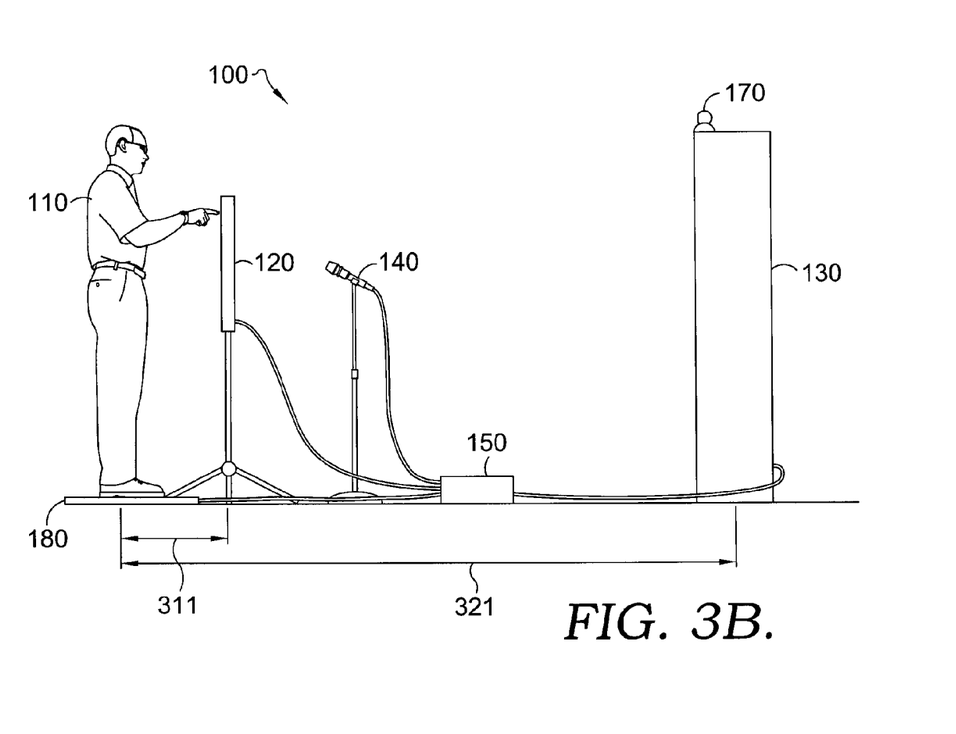
FIG. 3B further illustrates a system for near far testing in accordance with the present invention.

Referring now to FIG. 3B, system 100 is illustrated with near display device 120 located at another exemplary distance relative to subject 110. As illustrated in FIG. 3B, near display device 120 is located at a first distance 311 from subject 110, essentially at arm's length. Meanwhile, far display device 130 is located at a second distance 321 from subject 110.

Figure 3C:
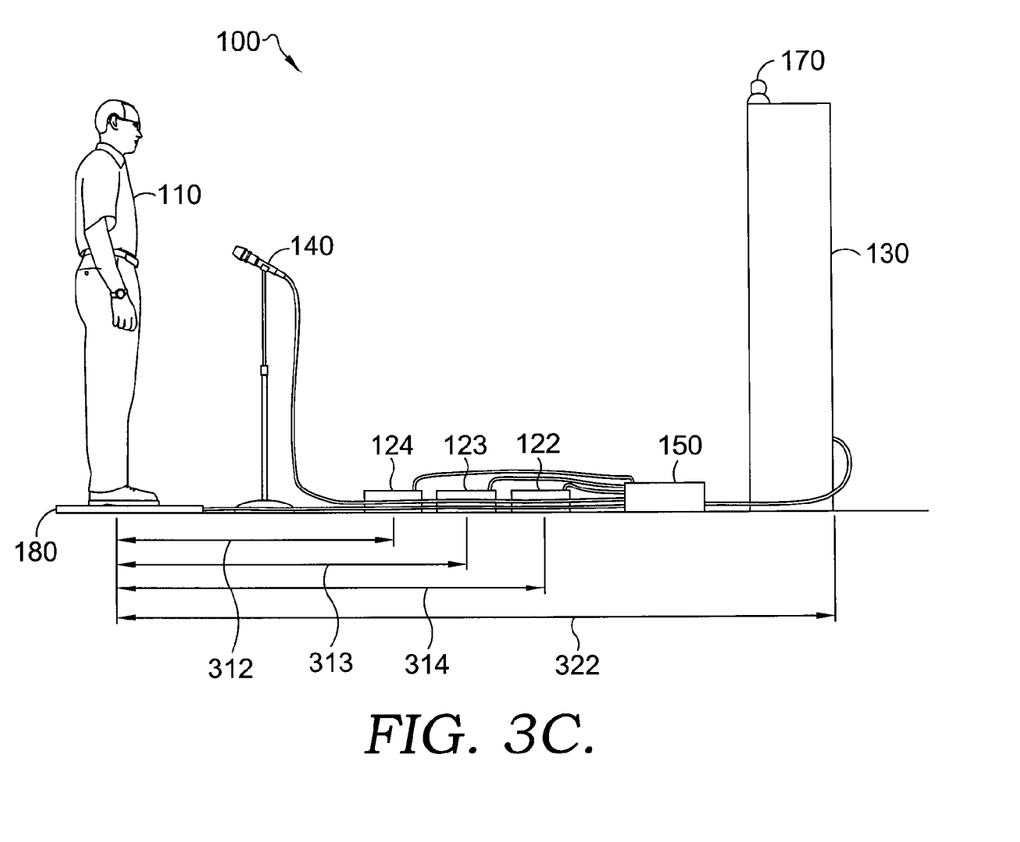
FIG. 3C further illustrates a system for near far testing in accordance with the present invention.

Referring now to FIG. 3C, system 100 is illustrated with a plurality of near display devices 121, 122, 123. As show in FIG. 3C, the plurality of near display devices 121, 122, 123 are oriented horizontally relative to subject 110. For example, near display devices 121, 122, 123 may be positioned on the floor or ground, or may be located at differing heights oriented horizontally relative to subject 110. The first near display device 121 may be located at a first distance from subject 312, the second near display device 122 may be located at a second distance 313 from subject 110, and the third near display device 123 may be located at a third distance 314 from subject 110. Meanwhile, far display device 130 may be located at a fourth distance 322 from subject 110. As illustrated in FIG. 3C, a system 100 in accordance with the invention may further test and/or train a subject's ability to detect a displayed indicia from a number of possible display areas, such as multiple possible display devices. A similar configuration may be utilized with the far display device 130, with multiple far display devices in differing positions or orientations being utilized relative to subject 110.

Figure 4A:
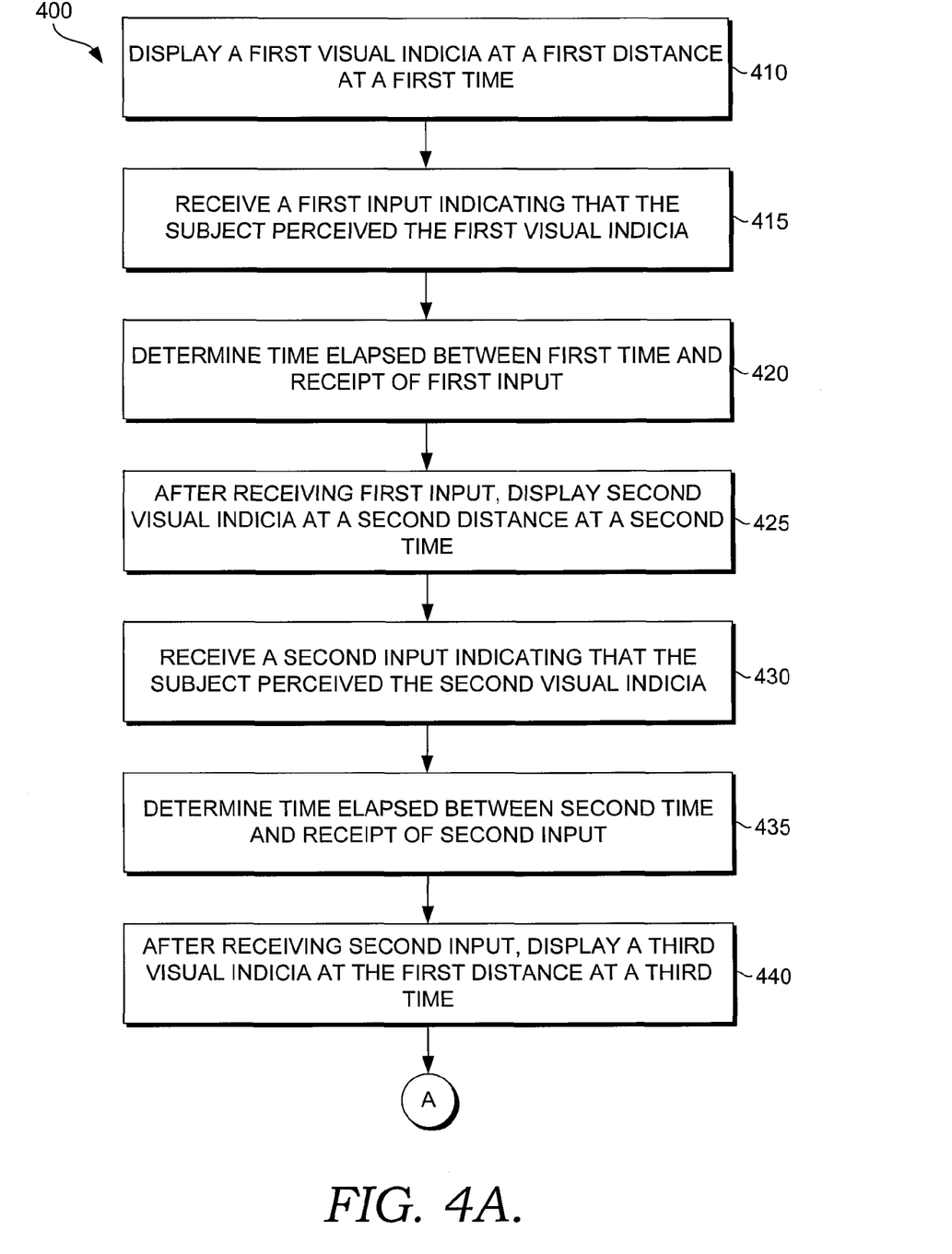
FIGS. 4A and 4B illustrate a method for near far testing in accordance with the present invention.
Figure 4B:
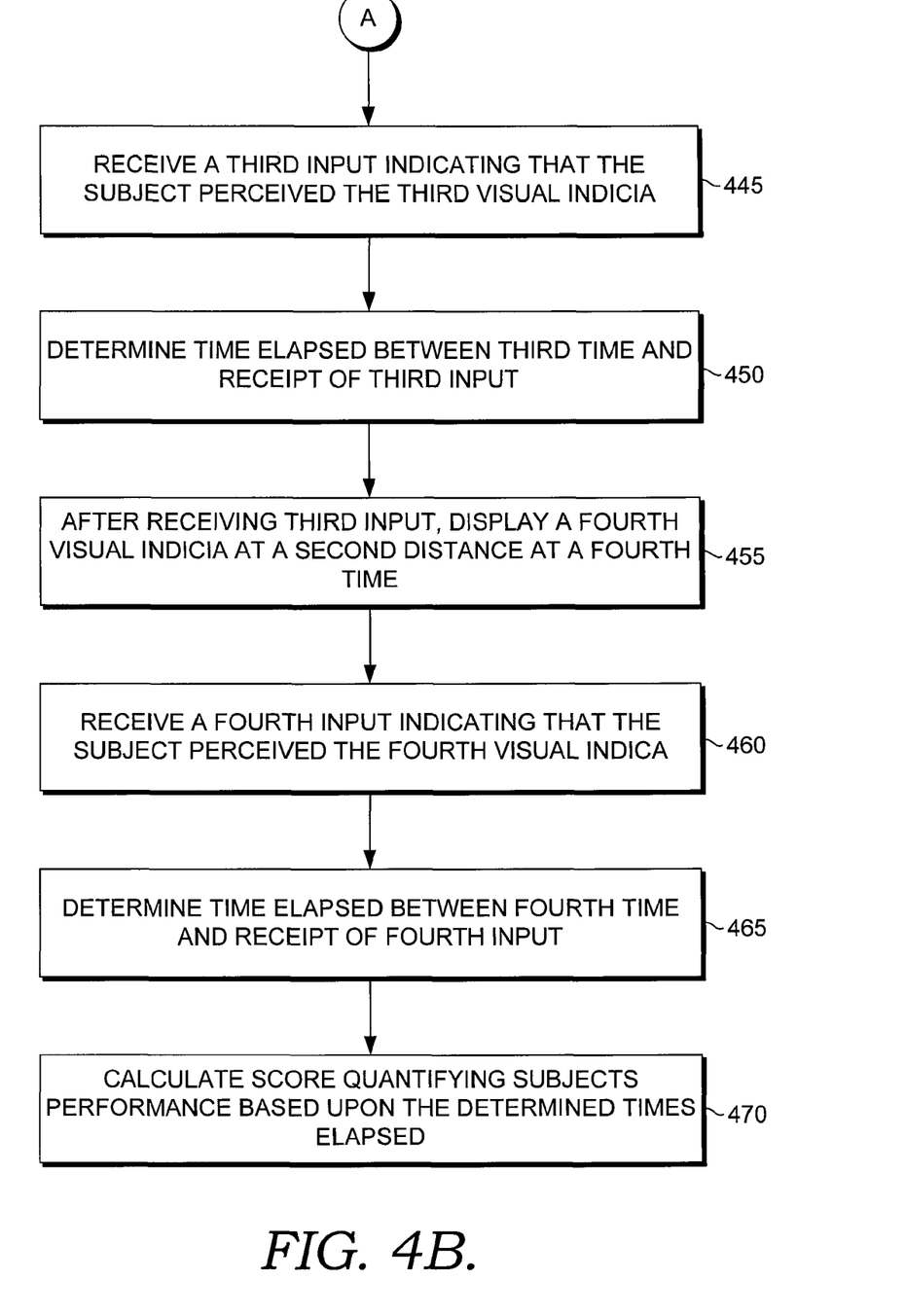

Referring now to FIG. 4A and FIG. 4B, a method 400 in accordance with the present invention is illustrated. In step 410 a first visual indicia may be displayed at a first distance at a first time. For example, step 410 may display a visual indicia on a near display device at a first time as illustrated in any of FIGS. 1-3C.

In step 415 a first input may be received indicating that the subject perceived the first visual indicia. Step 415 may, for example, utilize a microphone coupled to a testing unit to detect an input from a subject. The input may, for example, identify a characteristic possessed by a displayed indicia, such as the orientation of a Landolt C, the identity of a numeral or a letter, the identity of a displayed picture or photograph, the color of a displayed indicia, etc.

In step 420 the time elapsed between the first time at which the indicia was displayed and the receipt of the first input may be determined Step 420 may be appropriately performed by a testing unit that controls the display of the first visual indicia in step 410 and that operates in conjunction with a microphone to receive the first input in step 415.

In step 425, after receiving the first input a second visual indicia may be displayed at a second distance at a second time. For example, a visual indicia may be displayed at a far display device at a second time. In step 430 a second input may be received indicating that the subject perceived the second visual indicia.

Step 430 may resemble step 415 in terms of the types of inputs that may be received and the manner in which the input may be received, although one of ordinary skill in the art will appreciate that the characteristic, if any, identified for the displayed indicia may differ based upon the characteristic possessed by different displayed indicia.

In step 435, the time elapsed between the second time at which the second visual indicia was displayed and the receipt of the second input may be determined. Step 435, as with step 420, may be appropriately performed by a testing unit.

In step 440, after receiving a second input a third visual indicia may be displayed at the first distance and at a third time. For example, step 440 may display a third indicia on the near display device after a subject has responded in step 430 to a displayed indicia on the far display device.

In step 445 a third input may be received indicating that the subject perceived the third visual indicia. Step 445 may resemble step 415.

In step 450, the time elapsed between the third time at which the third indicia was displayed and the receipt of the third input may be determined. Step 450 may resemble step 420.

In step 455, after receiving the third input a fourth visual indicia may be displayed at a second distance and at a fourth time. For example, step 455 may display a fourth visual indicia at the far display device after receiving an input responsive to the display of the third visual indicia on the near display device. Step 455 may resemble step 425.

In step 460, an input may be received indicating that the subject perceived the fourth visual indicia. Step 460 may resemble step 430. In step 465 the time elapsed between the fourth time and the receipt of the fourth input may be determined. Step 465 may resemble step 435.

In step 470 a score may be calculated quantifying the subject's performance based upon the determined times elapsed. One skilled in the art will appreciate that further iterations of displays of indicia and receipts of appropriate inputs, along with a determination of elapsed times, may be performed prior to the performance of step 470. Step 470 may indicate, for example, that a subject responds slowly to indicia displayed at a first distance but does not respond slowly to the display of indicia at a second distance, which would be indicative of a subject with focusing or vergence difficulties at the first distance but not at the second distance.

Figure 5A:
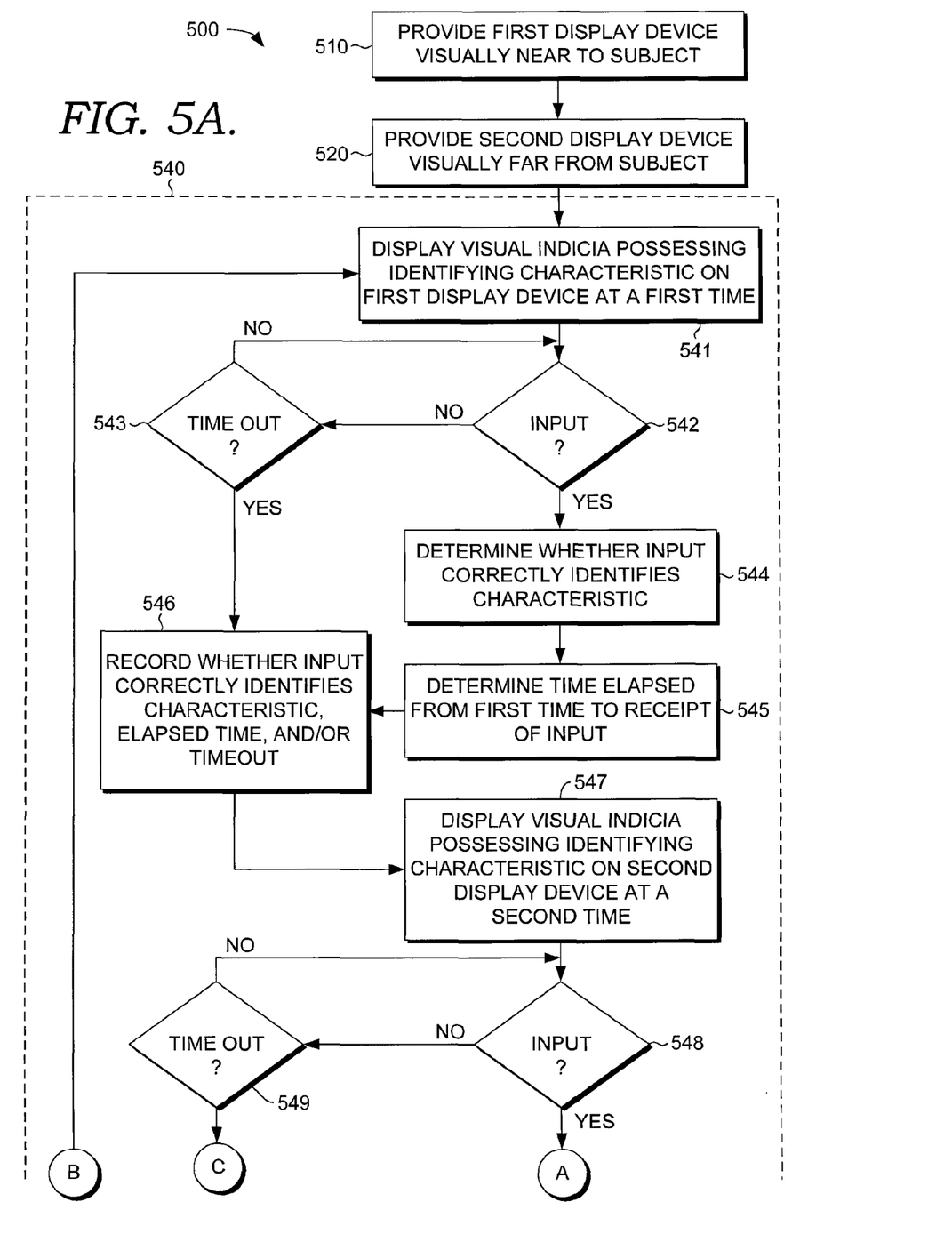
FIGS. 5A and 5B illustrate a further method for near far testing in accordance with the present invention.
Figure 5B:
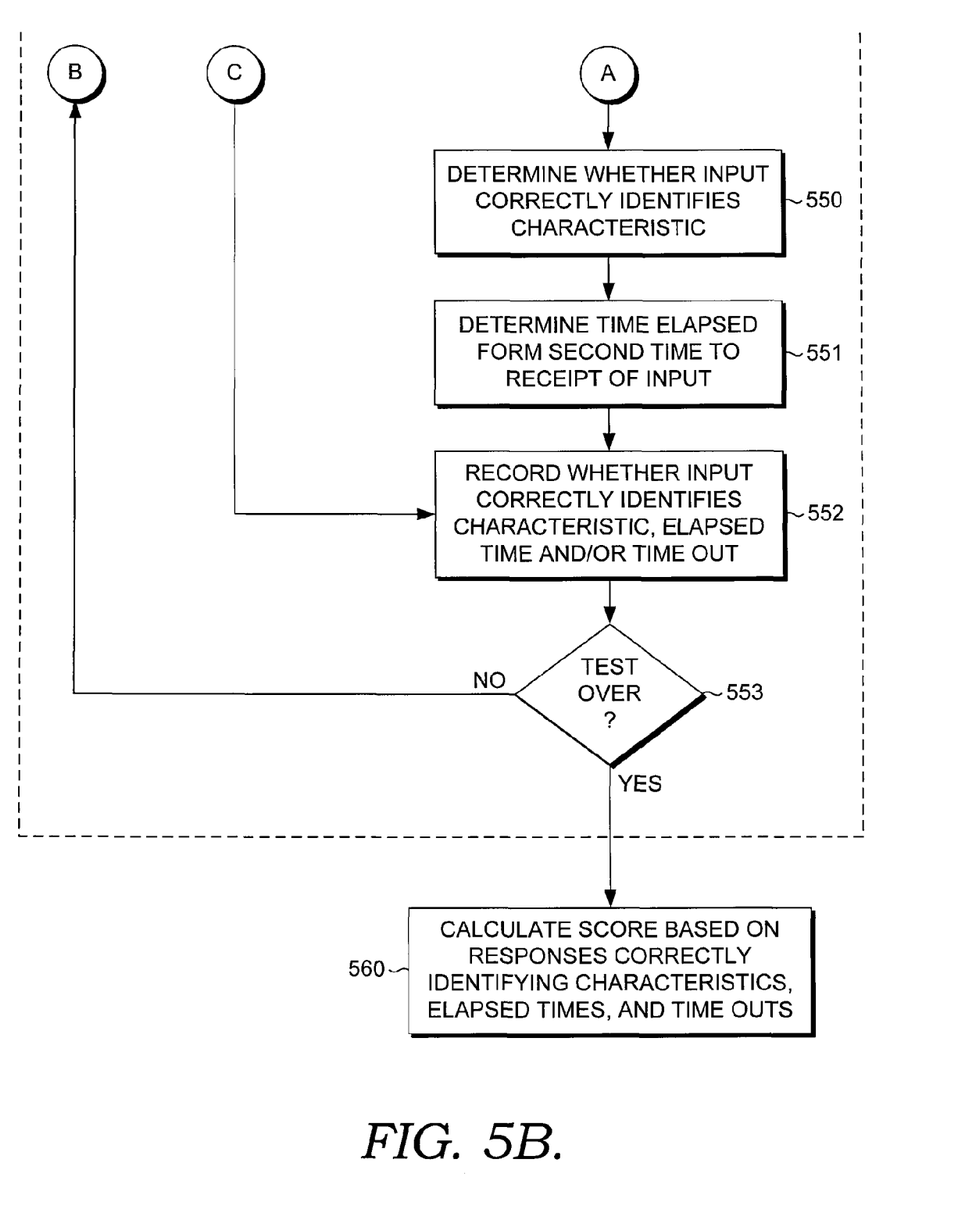

Referring now to FIGS. 5A and 5B, a further method 500 in accordance with the present invention is illustrated. In step 510 a first display device visually near to a subject may be provided. In step 520 a second display device visually far from the subject may be provided. Step 520 may provide a display device at or near optical infinity from a subject.

In testing/training step 540, which may comprise a number of sub-steps, a visual indicia may be displayed on the display devices and inputs may be received until testing/training has concluded. In sub-step 541 a visual indicia possessing an identifying characteristic may be displayed on the first display device at a first time. Sub-step 542 determines whether an input has been received from a subject. Step 542 may be performed, for example, by a testing unit in conjunction with a microphone. If the result of sub-step 542 is that no input has been received a timeout determination may be made in sub-step 543. The timeout determination of sub-step 543 may be made, for example, by a testing unit. If no timeout has been reached in sub-step 543, method 500 may continue to wait for an input in sub-step 542. If a timeout determination is made in sub-step 543, method 500 may proceed to sub-step 546, which will be described subsequently. If in sub-step 542 an input is received, method 500 may proceed to sub-step 544. Sub-step 544 determines whether the input correctly identifies the characteristic of the displayed indicia. For example, the displayed indicia may have a given orientation, identity, color, or other trait that may be identified in the input. Method 500 may then proceed to sub-step 545 to determine the time elapsed from the first time to receipt of the input in sub-step 542. Method 500 may then proceed to sub-step 546, which may also be reached as a result of a timeout decision in sub-step 543. In sub-step 546 whether a input correctly identified a characteristic, the elapsed time prior to receiving the input, and/or whether a timeout occurred may be recorded. Sub-step 546 may be performed, for example, by a testing unit and may utilize an electronic recording media such as a hard drive, memory, removable storage such as a compact disk, a DVD, a floppy disk, printing to a physical media such as paper, or other type of recording device. Method 500 may thereafter proceed to sub-step 547 of displaying a visual indicia possessing an identifying characteristic on the visually far display device at a second time. Method 500 may then proceed to sub-step 548, which determines whether an input has been received. Sub-step 548, like sub-step 542, may be performed by a testing unit in conjunction with a microphone. If the conclusion of sub-step 548 is that no input has been received, method 500 may proceed to sub-step 549 of determining whether a timeout has occurred. If no timeout has occurred, method 500 may return to sub-step 548 of determining whether an input has been received. Sub-step 549 may, for example, be performed by a testing unit, as was sub-step 543. If the result of sub-step 548 was to determine that an input was received, method 500 may proceed to sub-step 550. Sub-step 550 determines whether an input correctly identified the characteristic of the displayed indicia. Method 500 may then proceed to sub-step 551, which determines the time elapsed from the second time to the receipt of the input. Method 500 may then proceed to sub-step 552, which may also be reached if the conclusion of sub-step 549 is that a timeout has occurred. Sub-step 552 may record whether an input correctly identified the characteristic, record the elapsed time and/or record that a timeout occurred. As with sub-step 546, sub-step 552 may be performed by testing unit using any kind of recording media. Method 500 may then proceed to sub-step 553 to determine whether a test or training session has concluded. If the outcome of sub-step 553 is that the test/training is not over, method 500 may return to sub-step 541 and then the testing/training may continue. If the result of sub-step 553 is the conclusion that the test/training has concluded, testing step 540 may conclude and method 500 may proceed to step 560, which calculates a score based on responses correctly identifying characteristics, the elapsed times, and timeouts. A score may particularly identify the performance of a subject at a given distance. One skilled in the art will further appreciate that method 500 may utilize additional display devices at additional distances and directions from subject. In such an embodiment, additional sub-steps would be included in testing step 540 for the display devices at additional distances.

These and other variations to the present invention's systems and methods will be apparent to those of ordinary skill in the art.

What is claimed is:

1. A method for testing or training the vision of a subject, the method comprising:

displaying a first visual indicia at a first distance from the test subject at a first time;

receiving a first input indicating that the test subject perceived the first visual indicia;

displaying a second visual indicia at a second distance from the test subject at a second time only after receiving the first input indicating that the test subject perceived the first visual indicia, the second distance differing significantly from the first distance;

receiving a second input indicating that the test subject perceived the second visual indicia;

determining a time elapsed between the first time and the receipt of the first input;

determining a time elapsed between the second time and the receipt of the second input; and calculating a score quantifying a performance of the subject using the determined times elapsed.

2. The method for testing or training the vision of a subject of claim 1, the method further comprising:

displaying a third visual indicia at the first distance from the test subject at a third time after receiving the second input indicating that the test subject perceived the second visual indicia; and receiving a third input indicating that the test subject perceived the third visual indicia.

3. The method for testing or training the vision of a subject of claim 2, the method further comprising:

displaying a fourth visual indicia at the second distance from the test subject at a fourth time after receiving the third input indicating that the test subject perceived the third visual indicia; and receiving a fourth input indicating that the test subject perceived the fourth visual indicia.

4. The method for testing or training the vision of a subject of claim 3, the method further comprising:

determining a time elapsed between the third time and the receipt of the third input; and determining a time elapsed between the fourth time and the receipt of the fourth input.

5. The method for testing or training the vision of a subject of claim 1, where each input is a spoken input.

6. A method for testing or training the vision of a subject, the method comprising:

(a) providing a first display device visually near to the subject;

providing a second display device visually far from the subject;

(b) alternatively displaying visual indicia on the first display device and the second display device, alternatively displaying visual indicia comprising:

(1) displaying a visual indicia on the first display device at a first time;

(2) receiving a first spoken input from the subject using an automated voice detection system, the first spoken input indicating that the subject correctly perceived the visual indicia displayed on the first display device;

(3) determining a time elapsed between the first time and the receipt of the first spoken input;

(4) after receiving a spoken input from the subject indicating that the subject correctly perceived the visual indicia displayed on the first display device, displaying a visual indicia on the second display device at a second time;

(5) receiving a second spoken input from the subject using an automated voice detection system, the second spoken input indicating that the subject correctly perceived the visual indicia displayed on the second display device;

(6) determining a time elapsed between the second time and the receipt of the second spoken input;

(7) after receiving a spoken input from the subject indicating that the subject correctly perceived the visual indicia displayed on the second display device, determining whether the test has concluded, (A) if the test has not concluded, returning to step (a);

(B) if the test has concluded, calculating a score quantifying the performance of the subject using the determined times elapsed.

7. The method for testing or training the vision of a subject of claim 6, wherein:

displaying a visual indicia on the first display device further comprises displaying a visual indicia possessing an identifying characteristic;

receiving a spoken input from the subject using an automated voice detection system, the spoken input indicating that the subject correctly perceived the visual indicia displayed on the first display device further comprises determining that the spoken input correctly identifies the identifying characteristic possessed by the displayed visual indicia;

after receiving a spoken input from the subject indicating that the subject correctly perceived the visual indicia displayed on the first display device, displaying a visual indicia on the second display device further comprises displaying a visual indicia possessing an identifying characteristic; and receiving a spoken input from the subject using an automated voice detection system, the spoken input indicating that the subject correctly perceived the visual indicia displayed on the second display device further comprises determining that the spoken input correctly identifies the characteristic possessed by the displayed visual indicia.

8. The method for testing or training the vision of a subject of claim 7, wherein the identifying characteristic possessed by displayed visual indicia comprises a directional orientation.

9. The method for testing or training the vision of a subject of claim 7, wherein the identifying characteristic possessed by the displayed indicia comprises a color.

10. The method for testing or training the vision of a subject of claim 7, wherein the identifying characteristic possessed by the displayed indicia is an alphanumeric identity.

11. A method for testing or training the vision of a subject, the method comprising:

(a) providing a first display device visually near to the subject;

(b) providing a second display device visually far from the subject; and (c) alternatively displaying visual indicia on the first display device and the second display device, alternatively displaying visual indicia comprising:

(1) displaying a first visual indicia possessing an identifying characteristic on the first display device at a first time;

(2) receiving a spoken input from the subject responding to the first visual indicia using an automated voice detection system;

(3) determining whether the spoken input correctly identified the characteristic possessed by the first visual indicia;

(4) if no spoken input is received within a predetermined amount of time after the first time, determining that the display of the first visual indicia has timed out;

(5) recording whether the spoken input correctly or incorrectly identified the characteristic possessed by the first visual indicia and whether the display has timed out;
(6) after either receiving a spoken input from the subject or determining that the display of the first visual indicia has timed out, displaying a second visual indicia on the second display device at a second time;
(7) receiving a spoken input from the subject responding to the second visual indicia using an automated voice detection system;
(8) determining whether the spoken input correctly identifies the characteristic possessed by the second visual indicia;
(9) if no spoken input is received within a predetermined amount of time after the first time, determining that the display of the second visual indicia has timed out;
(10) recording whether the spoken input correctly or incorrectly identified the characteristic possessed by the first visual indicia and whether the display has timed out; and
(11) after receiving a spoken input from the subject or determining that the display of the second visual indicia has timed out, determining whether the test has concluded and if the test has not concluded returning to step (a);
(12) if the test has concluded, calculating a score quantifying the performance of the subject based upon the number of spoken inputs correctly identifying the characteristics possessed by the displayed indicia.

12. The method for testing or training the vision of a subject of claim 11, wherein:

receiving a spoken input from the subject responding to the first visual indicia using an automated voice detection system further comprises:
(1) determining the elapsed time between the first time and the receipt of the spoken input;
(2) recording whether the spoken input correctly or incorrectly identified the characteristic possessed by the first visual indicia and whether the display has timed out further comprises recording the elapsed time between the first time and the receipt of the spoken input;
(3) receiving a spoken input from the subject responding to the second visual indicia using an automated voice detection system further comprises determining the elapsed time between the second time and the receipt of the spoken input; and
(4) recording whether the spoken input correctly or incorrectly identified the characteristic possessed by the first visual indicia and whether the display has timed out further comprises recording the elapsed time between the second time and the receipt of the spoken input.

13. The method for testing or training the vision of a subject of claim 12, wherein calculating a score quantifying the performance of the subject based upon the number of spoken inputs correctly identifying the characteristics possessed by the displayed indicia further comprises calculating a score quantifying the performance of the subject based upon the number of inputs correctly identifying the characteristics possessed by the displayed indicia and the time elapsed between the elapsed times.

* * * * *